United States Patent
Steffens (10) Patent No.: US 9,859,994 B2
(45) Date of Patent: Jan. 2, 2018

(54) METHOD AND DEVICE FOR THE ADJUSTMENT OF CONTACTLESS DATA LINKS

(71) Applicant: Schleifring und Apparatebau GmbH, Fürstenfeldbruck (DE)

(72) Inventor: Holger Steffens, München (DE)

(73) Assignee: SCHLEIFRING UND APPARATEBAU GMBH, Fürstenfeldbruck (DE)

( * ) Notice: Subject to any disclaimer, the term of this patent is extended or adjusted under 35 U.S.C. 154(b) by 0 days.

(21) Appl. No.: 14/924,877

(22) Filed: Oct. 28, 2015

(65) Prior Publication Data

US 2016/0127052 A1 May 5, 2016

(30) Foreign Application Priority Data

Nov. 4, 2014 (EP) .................................... 14191716

(51) Int. Cl.
*H04B 1/00* (2006.01)
*H04B 15/00* (2006.01)
(Continued)

(52) U.S. Cl.
CPC ......... *H04B 17/0085* (2013.01); *A61B 6/032* (2013.01); *A61B 6/035* (2013.01);
(Continued)

(58) Field of Classification Search
CPC .................................................. H04B 17/0085
(Continued)

(56) References Cited

U.S. PATENT DOCUMENTS 7,079,619 B2 * 7/2006 Katcha ................... A61B 6/032
378/15
7,274,765 B2 * 9/2007 Krumme ................. A61B 6/56
378/15
(Continued)

FOREIGN PATENT DOCUMENTS

| EP | 1041785 A1 * | 4/2000 | ............ H04L 27/06 |
|---|---|---|---|
| EP | 1041758 | 10/2000 | |
| EP | 1041785 A2 | 10/2000 | |

OTHER PUBLICATIONS

Extended European Search Report in European Application No. 14191716.1.

*Primary Examiner* — Tilahun B Gesesse (74) *Attorney, Agent, or Firm* — Norton Rose Fulbright US LLP (57) ABSTRACT

A test setup for testing a contactless digital rotary joint integrated in a device requiring data transmission between a rotating part and a stationary part, the rotary joint further comprises a transmitter and a receiver. The transmitter has a transmitter amplifier, which is coupled to a pair of transmission lines, which are terminated by a pair of terminations. The transmission lines are differential transmission lines comprising a pair of conductors which is driven by differential signals from the transmitter amplifier. The receiver has a receiver antenna comprising a pair of antenna sections which are differentially operated and feed a differential signal to the receiver amplifier. A transmitter ground and a receiver ground are coupled to a common mode signal generator generating a common mode signal. A data source is coupled to the transmitter amplifier feeding a test signal into the transmitter amplifier, and a data sink is coupled to the receiver amplifier for receiving the test signal and generating a test result value. Also disclosed is a method for adjusting a contactless data link integrated in a device requiring data transmission between a rotating part and a stationary part.

13 Claims, 4 Drawing Sheets

(51) Int. Cl.

| | | |
|---|---|---|
| *H04B 17/00* | (2015.01) | |
| *H04B 17/309* | (2015.01) | |
| *A61B 6/03* | (2006.01) | |
| *A61B 6/00* | (2006.01) | |
| *H04B 5/00* | (2006.01) | |
| *H04B 17/10* | (2015.01) | |
| *H04B 17/14* | (2015.01) | |
| *H04B 17/16* | (2015.01) | |
| *H04B 17/21* | (2015.01) | |
| *H04B 17/27* | (2015.01) | |

(52) U.S. Cl.
CPC .............. *A61B 6/56* (2013.01); *H04B 5/0031* (2013.01); *H04B 5/0037* (2013.01); *H04B 17/104* (2015.01); *H04B 17/14* (2015.01); *H04B 17/16* (2015.01); *H04B 17/21* (2015.01); *H04B 17/27* (2015.01); *H04B 17/309* (2015.01); *A61B 6/5258* (2013.01)

(58) Field of Classification Search
USPC ........................... 455/67.1, 63.1, 226.1, 11.1
See application file for complete search history.

(56) References Cited

U.S. PATENT DOCUMENTS

| | | | | |
|---|---|---|---|---|
| 7,423,257 | B2* | 9/2008 | Popescu | A61B 6/035 250/227.14 |
| 7,502,438 | B2* | 3/2009 | Nakagawa | A61B 6/4233 378/15 |
| 7,760,851 | B2* | 7/2010 | Festag | A61B 6/56 378/15 |
| 7,889,836 | B2* | 2/2011 | Popescu | H01Q 3/02 378/15 |
| 7,957,786 | B2* | 6/2011 | Katcha | A61B 6/56 336/145 |
| 8,295,431 | B2* | 10/2012 | Lindorfer | A61B 6/56 378/15 |
| 8,594,480 | B2* | 11/2013 | Krumme | A61B 6/56 333/113 |
| 2003/0185427 | A1* | 10/2003 | Hsieh | A61B 6/56 382/131 |
| 2008/0202237 | A1 | 8/2008 | Hammerschmidt | |
| 2009/0026266 | A1* | 1/2009 | Raggam | G06K 7/0008 235/439 |
| 2013/0266026 | A1* | 10/2013 | McCormack | G06F 13/00 370/474 |
| 2014/0218132 | A1 | 8/2014 | Chen | |

* cited by examiner

METHOD AND DEVICE FOR THE ADJUSTMENT OF CONTACTLESS DATA LINKS

PRIORITY CLAIM

This application claims priority to pending European Application No. 14191716.1 filed on Nov. 4, 2014, which is incorporated herein by reference in its entirety.

BACKGROUND OF THE INVENTION

1. Field of the Invention

The invention relates to contactless data links which are used for transmission of high frequency signals or data between units movable against each other, which for example are rotating units like rotary joints. These contactless data links have to be adjusted or the adjustment has to be checked to meet the requirements of EMC standards, and to obtain a high data rate, high reliability, and low transmission losses or bit error rates. These adjustment procedures require specific tools and must be adapted to the contactless data links.

2. Description of Relevant Art

A contactless data link is disclosed in the U.S. Pat. No. 6,301,324 B1. This contactless data link is also called a contactless slip ring. It has a circular-shaped transmission line like a stripline at the rotating part which is coupled to a transmitter. The stationary part is a small receiver arranged in close proximity to the transmission line. The data rate is limited to about 2 Gb per second, which can be estimated from the disclosed bandwidth filter having a frequency range between 500 MHz and 1 GHz. For higher data rates, the transmission line may be modified as disclosed in EP 1 012 899 A. Here instead of a stripline, a pattern of narrower and wider sections is used. This pattern has a bandpass characteristic which suppresses unwanted noise.

SUMMARY OF THE INVENTION

The embodiments are based on the object of providing a contactless data link having an increased data rate while providing a higher noise immunity and increased EMS (electromagnetic suppression) performance. Another problem to be solved is to provide means and methods for adjusting a contactless data link at an increased data rate while providing a higher noise immunity and increasing EMS performance.

After a contactless data link has been built or integrated into in a device requiring data transmission between a rotating part and a stationary part, it may be adjusted to optimize noise immunity and increase EMS performance. Such devices may be CT (computed Tomography) scanners, industrial machines, vehicles and others. A contactless data link comprises a transmitter and a receiver. The transmitter may be at the rotating part of a CT scanner while the receiver may be at the stationary part. The transmitter preferably comprises an insulated base which may further comprise a dielectric material like polytetrafluoroethylene, a ceramic material, or any standard printed circuit board material, which may be fiber reinforced epoxy. Thereon is at least one transmission line comprising at least one transmitter conductor which may be a stripline-like conductor or any structure known from the prior art. Preferably, the transmission line is a differential structure comprising two transmitter conductors which are driven by differential signals. The transmitter further comprises at least one transmitter amplifier which feeds signals into the at least one transmission line. Preferably, the transmitter amplifier has impedance matching means. It is further preferred, if the transmitter further comprises at least one termination means at the end of the at least one transmission line, which is preferably opposite to the transmitter amplifier. Preferably a data source generating a stream of data is coupled to the transmitter amplifier.

The receiver is mounted in close proximity to the transmitter without touching the transmitter. It has at least one receiver antenna, which preferably has at least one antenna section matching and being mounted in close proximity to the at least one transmitter conductor or the at least one transmitter conductor. Due to the close proximity, signals are coupled between the at least one transmission line and the receiver antenna, which are further amplified by at least one receiver amplifier and coupled to a data sink. Although the minimum component of the receiver is the receiver antenna, it is preferred to include at least one receiver amplifier into the receiver to obtain minimal signal path lengths between the antenna and the amplifier. Preferably, the receiver has a receiver antenna comprising a first antenna section and a second antenna section which are differentially operated and feed a differential signal to the receiver amplifier.

In a preferred embodiment of a CT scanner rotary joint, the transmitter and therefore the conductors attached thereto are rotating, whereas a receiver is stationary at the stationary part. In an alternative embodiment, the transmitter may be at the stationary part, where the receiver is at the rotating part. To achieve a bidirectional communication, both embodiments may be combined. Generally, the receiver must be aligned to the conductors, such that the best signal transmission quality and the best EMC performance is achieved.

In a preferred embodiment, a test setup also called a test device for adjusting or for checking the adjustment of the receiver versus the transmitter comprises at least one test pattern generator. Preferably, the test setup is used for checking and/or adjusting the spatial relationship between a receiver antenna and transmission lines of a contactless data link. A test pattern generator may be a separate unit coupled to the transmitter amplifier feeding the test signal into the conductors. It may also be part of the transmitter, or it may be a software generating a test pattern within the transmitter. Preferably, the test pattern is a pseudo-noise signal. It may be any other suitable pattern. Most preferably, the test pattern has a similar bandwidth and similar spectral characteristics as normal application data. A test setup preferably comprises a common mode signal generator which is coupled between a ground of the transmitter and a ground of the receiver. The generator voltage is common to both conductors of the differentially driven transmission line. The common mode signal may further be coupled into a rotor and/or a stator and/or a bearing between the rotor and the stator of a rotary joint and/or a CT scanner. The common mode signal preferably is a narrow band sinusoidal signal which may be swept to determine any frequency dependence of the measuring results. It may also be any other signal, e.g. a broad band signal like a pseudo-noise signal or a signal which simulates the behavior of signals in a real operating device, like a CT scanner. It may be any other signal, which is known to affect data transmission. Such a signal may be for example noise generated by the X-ray generator or by a contactless power transformer.

It is further preferred, if a common mode choke is provided in the power supply lines of the transmitter and/or the receiver.

It is further preferred, if a means for holding the receiver in a defined position relative to the transmitter and for precisely adjusting the relative position between the receiver and the transmitter is provided.

For adjustment of the receiver, the signal quality at the receiver is determined. This is preferably done by measuring the bit error rate, preferably by comparing the received signal with the predetermined pattern. Alternatively the signal quality can be obtained by measuring the jitter value of the signal received. For describing the alignment steps, an orthogonal coordinate system is used, which is referenced to the center of the receiver antenna, which is part of the receiver. The x-axis is parallel to a tangent to the transmission lines, corresponding to the direction (or the inverse direction) of rotation. The y-axis is parallel to the rotation axis. The z-axis is radial to the transmitter. The alignment of the receiver is adjusted as follows:
 a) The receiver is adjusted in its height above the transmitter, parallel to the z-axis.
 b) The receiver is adjusted parallel to the y-axis.
 c) The receiver is tilted around the x-axis.
 d) The receiver is tilted around the z-axis.
 e) The receiver is tilted around the y-axis.

Preferably, step a) is performed as the first step, as the height is mainly determined by mechanical characteristics, such that the transmitter never touches the receiver during operation, which may result in damage of the parts. The further steps b) to e) may be performed in any order. It is preferred, if for each of these further adjustment steps, the settings are adjusted in small steps and the resulting signal quality or bit error rate is measured. Based on this result, the best setting may be calculated. It may be beneficial to iterate steps b) to e) to obtain the best result. It may further be beneficial to include step a) into iteration. This may avoid the receiver approaching the transmitter too close. It may be possible to omit unnecessary steps. Preferably step b) is omitted, as this kind of alignment may easily be done by the mechanical design of the receiver.

As well adjusted data links have very low bit error rates, which may be in an order of 10E-15, the measuring time until a single bit error occurs may be several hours. This is far too long for a useful method in manufacturing. Therefore, preferably measurement is aborted, if a certain predetermined bit error rate like 10E-10 is achieved or if after the transmission of a predetermined number of bits no bit error has occurred. This may result in a measuring time of one second or a few seconds. If the misalignment is large enough, the bit error rate will grow to significantly larger values. For determining the optimum point, these curves may be extrapolated to determine the point of minimum or in a simpler method, only the center between the positive deviation resulting in a predetermined bit error rate in or above a predetermined bit error rate, and the negative deviation resulting in or above a predetermined bit error rate is used. By this method, comparatively quick measurements may be performed.

The same may apply to a jitter measurement. The optimum adjustment may either be derived by extrapolating data or by creating a pass/fail criteria by comparing the test result (e.g. bit error rate or jitter) with a predetermined threshold value.

Also other signal quality measurements are possible especially those creating a pass/fail result like checksum violations as used with FEC (forward error correction).

In addition the voltage level of the common mode noise may be increased during the adjustment steps since the EMS is increased with the increased quality of the mechanical adjustment. By doing so also the region where a pass criteria is met can be reduced and the optimum adjustment can be found without inter- or extrapolation.

The test setup or test device consisting of test pattern generator, common mode signal generator, common mode chokes and signal quality measurement and evaluation may be a device to be added to the system only during adjustment or it might also be already partially implemented as part of receiver and antenna or as part of the communication infrastructure of the system.

The mechanical adjustment of the receiver may be part of the receiver mount and may be either operated manually or automatically e.g. by spindle drives.

The adjustment procedure preferably is controlled and operated manually during assembly or service but also an automatic control is possible which controls the spindle drives.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
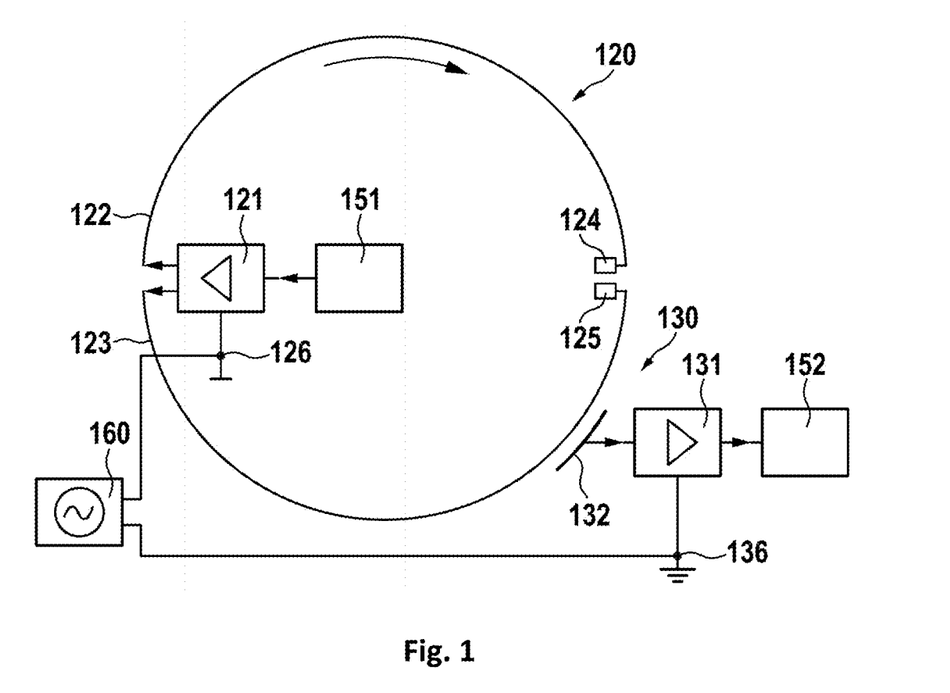
FIG. 1 shows a basic test setup.

In FIG. 1, a preferred embodiment is shown. The contactless rotary joint has a transmitter 120 and a receiver 130. A data source 151 generating a test pattern which preferably is a pseudo-noise pattern is coupled to a transmitter amplifier 121 which is part of the transmitter 120. The transmitter amplifier is generating signals for driving the transmission lines 122, 123. These are terminated by terminators 124, 125. Preferably, the transmission lines 122, 123 have the same length and enclose half of the circumference of the rotating part of the rotary joint. It is further preferred, if the terminators 124, 125 are opposite to the position to where the transmitter amplifier 121 is connected to the transmission lines 122, 123. As will be shown later, each of the transmission lines 122, 123 is a differential line comprising two transmitter conductors 127, 128 which are driven by a differential signal.

A receiver 130 is mounted in close proximity to the transmitter 120 and has a receiver antenna 132 which couples a receiving signal to receiver amplifier 131. The output signal of this receiver amplifier 131 is fed to a data sink 152, which evaluates the signal transmission quality. It is preferred, if the receiver and/or the data sink 152 generates a bit error rate count value. The transmitter 120 has a transmitter ground 126, which may be the rotating part ground. Most of the rotating part's signals are referenced to that ground, which preferably is the base of a large metal disk bearing the rotating components. The receiver has a receiver ground 136 which may also be the stationary part ground. Preferably, most of the stationary circuits are connected to a common metal frame structure bearing the stationary part of a CT scanner gantry.

A common mode signal generator 160 is connected between the transmitter ground 126 and the receiver ground 136. It generates a common mode signal there between. This common mode signal also applies to each pair of the differential lines of the transmission lines 122, 123, and therefore generates a common mode voltage at the receiver antenna 132. This signal may be a sinusoidal signal. The signal amplitude may be 30 Volts and the frequency range may be between 50 Hz and 50 MHz. Only if the receiver antenna is perfectly adjusted, the common mode suppression has its maximum value, and therefore, the common mode noise immunity of the receiver or the whole data link has its maximum value.

Figure 2:
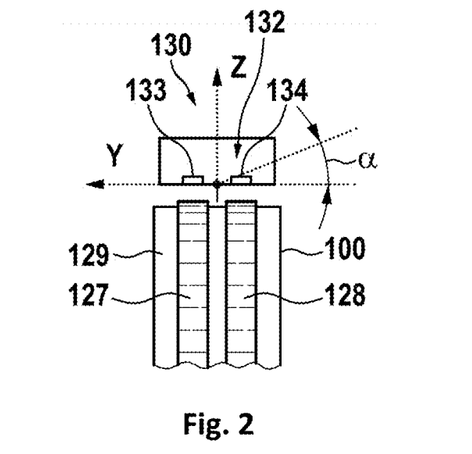
FIG. 2 shows a first view of the receiver along the x-axis.

In FIG. 2, a first view of the receiver 130 mounted above the transmitter conductors 127, 128 is shown along the x-axis. The transmitter conductors 127, 128 are mounted to the rotating part 100 of a CT scanner gantry. They preferably have an insulated base 129, which preferably is a dielectric carrier, which may be any insulating material like a ceramic, polytetrafluoroethylene, or any printed circuit board material, which for example may be based on fiber-reinforced epoxy. There are two transmitter conductors 127, 128 which are fed by a differential signal and which may either belong to first transmission line 122 or second transmission line 123. Here, the receiver 130 is only symbolized. It has preferably a receiver antenna 132 comprising of a first antenna section 133 and a second antenna section 134 at its bottom side. These form a differential antenna receiving the differential signal transmitted by the differential transmitter conductors 127, 128. The receiver 130 may comprise the receiver amplifier 131 and/or the data sink 152. It is preferred to have the receiver amplifier 131 integrated into the same housing with the antenna sections 133, 134, as this may help to keep the contacting lines there-between as short as possible.

In a first step, the height along the z-axis of the receiver 130 and therefore the distance between transmitter and receiver is adjusted. Preferably, this distance is set to a predetermined distance which ensures, that there is no physical contact during rotation between the rotating and the stationary parts, as this may lead to a damage of the parts. After this step, all other steps may be performed in any sequence. A further step may be adjustment of the position of the receiver 130 parallel to the y-axis. Another step would be tilting of the receiver around the x-axis in an angle α. It is not necessary to adjust the receiver assembly along the x-axis, as there is a continuous movement during rotation.

Figure 3:
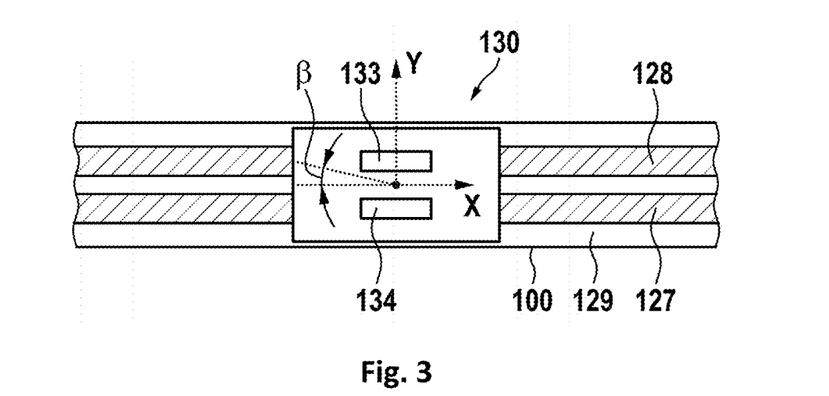
FIG. 3 shows a first view of the receiver along the z-axis.

In FIG. 3, a first view of the receiver along the z-axis is shown. Here, a further adjustment by tilting the receiver 130 around the z-axis for an angle β is shown.

Figure 4:
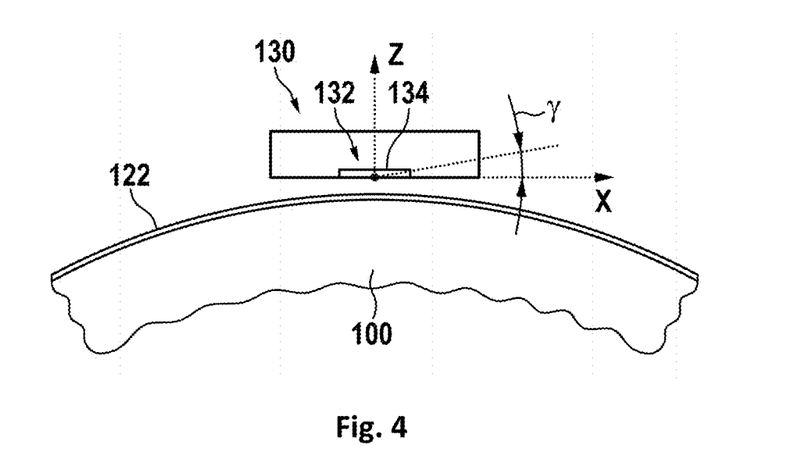
FIG. 4 shows a first view of the receiver along the y-axis.

In FIG. 4, a first view of the receiver along the y-axis is shown. Here, a further adjustment around the y-axis for an angle γ is shown.

Figure 5:
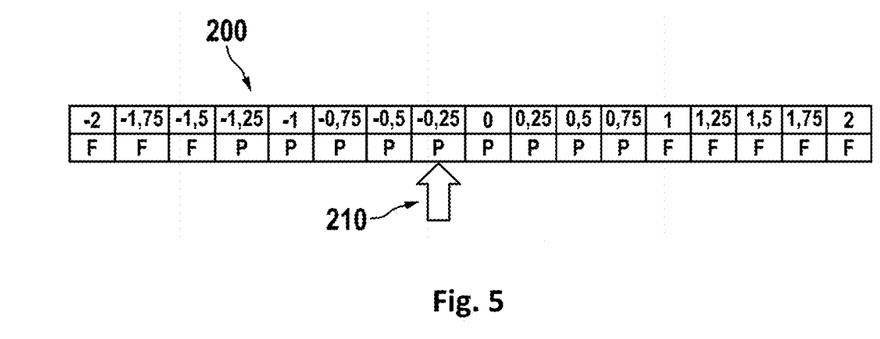
FIG. 5 shows a table with test results for the adjustment steps.

In FIG. 5, a table 200 with exemplary test results for any one of the previously mentioned adjustment steps is shown. The top row exemplarily shows the deviation from a center value, which for example may be the deviation of a tilting angle (α, β, γ) in degrees or a distance along the y-axis in mm. In the second row, there are letters "P", indicating that by this setting, the bit error rate was acceptable resulting in pass. The letter "F" indicates that by using these settings the bit error rate was too high and therefore, the test failed. The criteria for passing the test may be reaching a predetermined bit error rate. In this example, the center of the passed tests is used as the optimum setting which is at about −0.25, as indicated by arrow 210. Other methods may also be used as e.g. center of gravity method.

Figure 6:
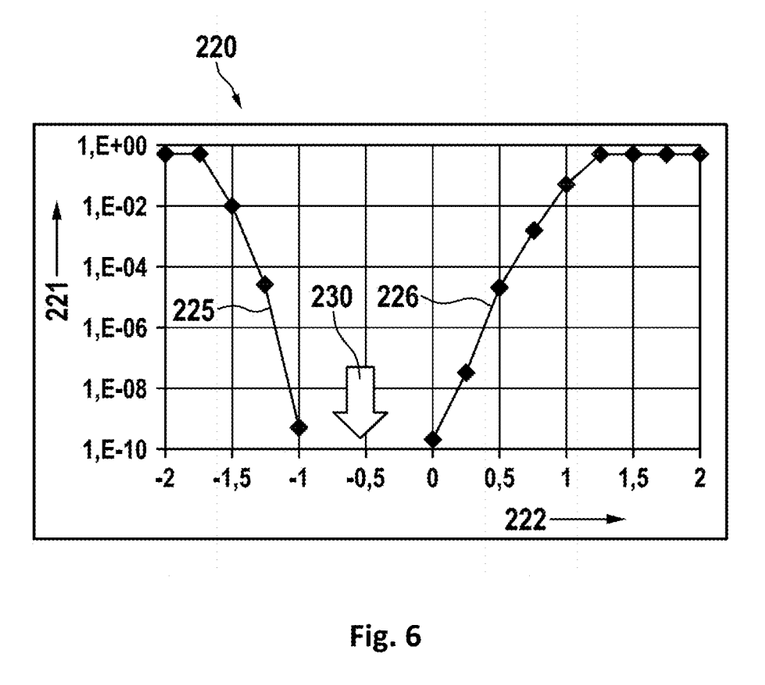
FIG. 6 shows another embodiment of an evaluation.

In FIG. 6, another embodiment of an evaluation for finding the optimum setting is shown. Here, the function of the bit error rate is drawn into a diagram 220. A first axis, which may be the horizontal axis 222, varies in this example from −2 to +2 units and shows the deviation which may again be in millimeters or in degrees, as explained with respect to the previous figure. A second axis 221 is used for indicating the bit error rate which varies in this example in a range of 1E0 to 1E-10. There is an exemplary curve of bit error rate having a left section 225 and a right section 226. In this example, measurement has been aborted if a bit error rate of 1E-10 has been reached or if 1E10 bits have been transmitted without any error. This was made to prevent excessive measuring times. For finding the optimum setting, the center between these two curves is selected, resulting in a position at approximately −0.6, indicated by arrow 230.

Figure 7:
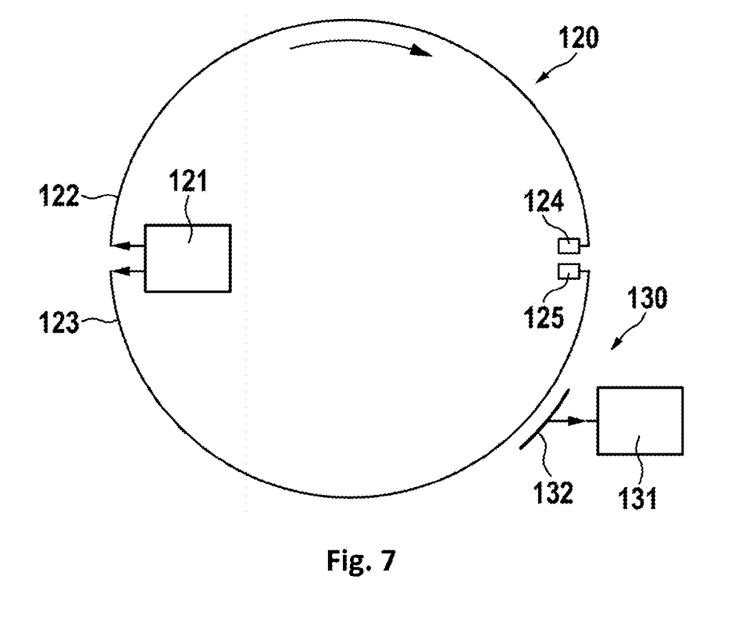
FIG. 7 shows the basic diagram of a contactless rotary joint.

In FIG. 7, the basic diagram of a contactless rotary joint as it is used in a CT scanner is shown. Most of the components already have been described. During operation, there is no common mode signal generator 160 as shown before. Furthermore, the transmitter amplifier 121 is fed by a data source (not shown), which may be the X-ray detector of the CT scanner. Furthermore, the receiver amplifier 131 delivers its signal to a data sink (not shown), which may be a data processing system and which preferably is an image reconstructor.

Figure 8:
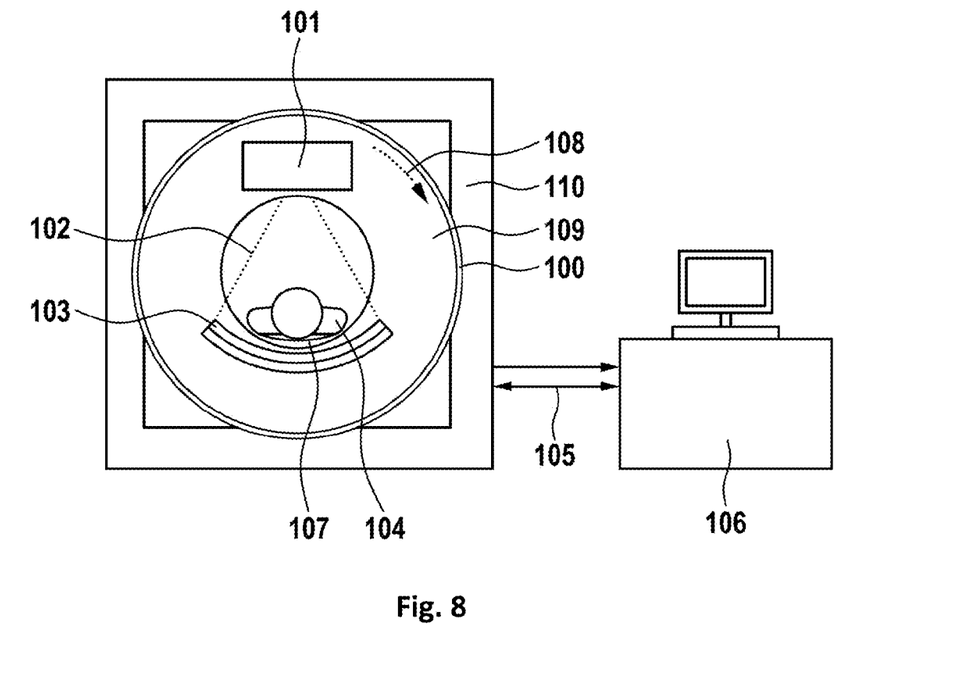
FIG. 8 schematically shows a CT scanner.

FIG. 8 shows a computer tomograph in which an example of a rotating contactless data link is used. The computer tomography (CT scanner) includes two basic components. A stationary part 110 serves as a base and support for the entire instrument in which a rotating part 109 rotates in rotation direction 108. A patient 104 is positioned on a bed 107 in an opening of the rotating part. An X-ray tube 101 and also a detector 103 disposed oppositely thereto are provided for scanning the patient by means of X-rays 102. The X-ray tube 101 and the detector 103 are disposed to be rotatable on the rotating part 109. A contactless rotary joint 100 comprises a rotating transformer or slipring for delivering electrical power to the rotating part and a contactless data link for transfer of the imaging data from the rotating detector 103 to the stationary part 110. An evaluation and control unit 106 serves for operating the computer tomograph and also for displaying the generated images. Communication with the computer tomograph is effected via a data link 105.

It will be appreciated to those skilled in the art having the benefit of this disclosure that this invention is believed to provide testing and adjustment means and methods for contactless rotating data links. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 rotary joint
101 X-ray tube
102 X-ray beam
103 X-ray detector
104 patient
105 stationary data link
106 evaluation and control unit
107 patient's bed
108 rotating direction
109 rotating part of computer tomograph
110 stationary part of computer tomograph
120 transmitter
121 transmitter amplifier
122, 123 transmission lines
124, 125 terminators
126 transmitter ground
127, 128 transmitter conductors
129 insulated base
130 receiver
131 receiver amplifier
132 receiver antenna
133, 134 antenna sections
136 receiver ground
151 data source
152 data sink
160 common mode signal generator
200 table
210 arrow indicating optimum setting
220 diagram of bit error rate
221 second axis
222 first axis
225 left section of bit error rate curve
226 right section of bit error rate curve
230 arrow indicating optimum setting

The invention claimed is:

1. A test apparatus for testing a contactless digital rotary joint integrated in a device requiring data transmission between a rotating part and a stationary part, the rotary joint comprising a contactless data link, the contactless data link comprising:
   a transmitter having a transmitter amplifier coupled to at least a first transmission line and a second transmission line which are respectively terminated by a first termination and a second termination, the first and second transmission lines being differential transmission lines respectively comprising a first conductor and a second conductor, the transmitter amplifier configured to provide differential signals to the first and second conductors, and
   a receiver configured to receive signals from the transmitter, the receiver having a receiver amplifier and at least one receiver antenna comprising at least a first antenna section and a second antenna section which are configured to be differentially operated to feed a differential signal to the receiver amplifier, wherein:
   a transmitter ground defined by the transmitter and a receiver ground defined by the receiver are coupled to a common mode signal generator that is configured to generate a common mode signal,
   a data source is coupled to the transmitter amplifier and configured to feed a predetermined test signal into the transmitter amplifier, and
   a data sink is coupled to the receiver amplifier and configured to receive the test signal from the receiver amplifier and generate a test result value.

2. The test apparatus according to claim 1, wherein the data source is configured to generate the test signal that comprises a pseudo-noise signal, and the data sink configured to generate a test result value that comprises a bit error rate value.

3. The test apparatus according to claim 1, wherein the common mode signal generator is configured to generate a sinusoidal signal that comprises a swept-frequency signal or a broad band signal.

4. The test apparatus according to claim 1, wherein the common mode signal generator is further coupled to one or more additional components selected from the group of components consisting of: a rotor, a stator, a bearing between a rotor and a stator of the rotary joint, and a CT scanner.

5. The test apparatus according to claim 1, wherein a common mode choke is provided in power supply lines of the transmitter, the receiver, or both the transmitter and the receiver.

6. The test apparatus according to claim 1, further comprising:
   a means for holding the receiver in a defined position relative to the transmitter and for precisely adjusting the position of the receiver relative to the transmitter, including: height of the receiver above the transmitter parallel to the z-axis, lateral position of the receiver parallel to the y-axis, tilt of the receiver around the x-axis, tilt of the receiver around the z-axis, and tilt of the receiver around the y-axis.

7. A method for adjusting a contactless data link integrated in a device requiring data transmission between a rotating part and a stationary part, the method comprising the steps of:
   connecting a data source to a transmitter amplifier of a transmitter,
   feeding a test signal from the data source to differential transmission lines of the transmitter to transmit the test signal, the differential transmission lines terminated by terminations at the rotating part,
   connecting a data sink to a receiver amplifier of a receiver, the receiver amplifier coupled to a receiver antenna of the receiver,
   receiving with the receiver the signals transmitted by the transmission lines of the transmitter,
   feeding a common mode signal from a common mode signal generator to a transmitter ground defined by the transmitter and to a receiver ground defined by the receiver, and
   adjusting a spatial relationship between the receiver antenna and the transmission lines.

8. The method according to claim 7, further comprising the steps of
   conducting a PASS/FAIL test,
   advancing to a further spatial position, and
   after having tested all positions of one dimension, evaluating the results to find an optimum position.

9. The method according to claim 7, wherein the test signal generated by the data source is a pseudo-noise signal, and the data sink generates a value indicating a bit error rate.

10. The method according to claim 7, wherein adjusting the spatial relationship between the receiver antenna and the transmission lines comprises one or more adjustments selected from the group of adjustments consisting of: relative position along a y-axis parallel to a rotation axis of the rotary joint, relative tilt about an angle $\alpha$ around a x-axis parallel to a tangent at the transmission lines, relative tilt about an angle $\beta$ around a z-axis radial to the transmission lines, and relative tilt about an angle $\gamma$ around the y-axis.

11. The method according to claim 7, wherein transmission of the test signal is terminated if a predetermined bit error rate has been measured.

12. The method according to claim 7, wherein transmission of the test signal is terminated if a predetermined number of bits have been transmitted without any transmission error.

13. The method according to claim 8, wherein the optimum position is determined by determining the center of a region which is limited by areas in which the measured bit error rate exceeds a predetermined threshold.

\* \* \* \* \*